(12) United States Patent
Kobayashi et al.

(10) Patent No.: US 6,897,460 B2
(45) Date of Patent: May 24, 2005

(54) ULTRAVIOLET PASTEURIZER

(75) Inventors: Susumu Kobayashi, Tokyo (JP); Masaru Horiguchi, Tokyo (JP)

(73) Assignee: Kabushiki Kaisha Top, Tokyo (JP)

( * ) Notice: Subject to any disclaimer, the term of this patent is extended or adjusted under 35 U.S.C. 154(b) by 65 days.

(21) Appl. No.: 10/275,402

(22) PCT Filed: May 16, 2001

(86) PCT No.: PCT/JP01/04071
§ 371 (c)(1),
(2), (4) Date: Nov. 5, 2002

(87) PCT Pub. No.: WO01/87363
PCT Pub. Date: Nov. 22, 2001

(65) Prior Publication Data
US 2003/0170152 A1 Sep. 11, 2003

(30) Foreign Application Priority Data
May 19, 2000 (JP) ........................................ 2000-148691

(51) Int. Cl.$^7$ ............................ G01J 00/00; G01J 1/00; G21F 5/02
(52) U.S. Cl. ............................... 250/504 R; 250/494.1; 250/498.1; 250/497.1; 250/496.1
(58) Field of Search ............... 76/223, 224; 250/455.11, 250/504 R, 494.1, 498.1, 497.1, 496.1

(56) References Cited

U.S. PATENT DOCUMENTS

| | | | | |
|---|---|---|---|---|
| 3,347,025 A | * | 10/1967 | Wiley ............................ | 96/224 |
| 4,100,415 A | * | 7/1978 | Blaisdell et al. ........ | 250/455.11 |
| 5,453,049 A | * | 9/1995 | Tillman et al. ............... | 454/228 |
| 5,616,172 A | * | 4/1997 | Tuckerman et al. ............ | 96/16 |
| 5,837,207 A | * | 11/1998 | Summers ...................... | 422/121 |
| 5,891,399 A | * | 4/1999 | Owesen ........................ | 422/121 |
| 5,908,742 A | * | 6/1999 | Lin et al. ........................ | 435/2 |
| 6,028,315 A | * | 2/2000 | Bailey et al. ........... | 250/455.11 |
| 6,039,928 A | * | 3/2000 | Roberts .................... | 422/186.3 |
| 6,494,940 B1 | * | 12/2002 | Hak ............................ | 96/224 |

FOREIGN PATENT DOCUMENTS

| JP | 44-5509 B1 | 3/1969 |
|---|---|---|
| JP | 63-135646 U | 9/1988 |

* cited by examiner

Primary Examiner—John R. Lee
Assistant Examiner—Kalimah Fernandez
(74) Attorney, Agent, or Firm—Birch, Stewart, Kolasch & Birch, LLP

(57) ABSTRACT

When an ultraviolet pasteurizer is used in a room free of a person, left and right light shield doors are opened to expose ultraviolet lamps outwardly. When an operation switch on a control panel is then turned on, an operation start timer is actuated, and the ultraviolet lamps are then energized to sterilize surrounding surfaces after elapse of 5 minutes. When the ultraviolet pasteurizer is used in a room occupied by a person, the left and right light shield doors are closed to direct the ultraviolet lamps inwardly until all light shield doors are brought into a substantially triangular prism. When the operation switch on the control panel is then turned on, the ultraviolet lamps and a fan are energized to draw external air from an air inlet. The drawn air passes through an inner radiation chamber defined inwardly of the light shield doors that have been combined into the substantially triangular prism. The air is sterilized by ultraviolet radiation emitted from the ultraviolet lamps and discharged from an air outlet.

13 Claims, 6 Drawing Sheets

ULTRAVIOLET PASTEURIZER

This application is the national phase under 35 U.S.C. § 371 of PCT International Application No. PCT/JP01/04071 which has an International filing date of May 16, 2001, which designated the United States of America.

TECHNICAL FIELD

The present invention relates to an ultraviolet pasteurizer for sterilizing an indoor space by the application of ultraviolet radiation.

BACKGROUND ART

Conventional ultraviolet pasteurizers for sterilizing an indoor space comprise an ultraviolet lamp that is energized to emit ultraviolet radiation to sterilize indoor walls and indoor air. The ultraviolet pasteurizers are basically classified into two types, i.e., one for applying ultraviolet radiation to indoor walls or the like and one for emitting ultraviolet radiation in a tubular member to sterilize indoor air that flows through the tubular member.

The former type of ultraviolet pasteurizer is disadvantageous in that since direct exposure to ultraviolet radiation is harmful to persons, no entry into the room is permitted while the ultraviolet pasteurizer is in operation or the application of ultraviolet radiation toward any person in the room needs to be inhibited.

The latter type of ultraviolet pasteurizer is also problematic in that it can sterilize microorganisms suspended in the air, but is unable to sterilize microorganisms attached to wall, ceiling, and floor surfaces.

It is therefore an object of the present invention to provide an improved ultraviolet pasteurizer which can be operated in different modes depending on whether there is a person in a room to be sterilized or not, for thereby solving the above problems.

DISCLOSURE OF THE INVENTION

To achieve the above object, there is provided an ultraviolet pasteurizer according to the first aspect of the present invention, comprising an ultraviolet lamp, a light shield door openable and closable to block or pass ultraviolet radiation emitted from the ultraviolet lamp, an inner radiation chamber definable inwardly of the light shield door so that ultraviolet is shut of f from outward by the light shield door, an air inlet and an air outlet providing communication between the inner radiation chamber and an external space, and a fan for introducing air from the external space via the air inlet into the inner radiation chamber, displacing the air near the ultraviolet lamp, and discharging the air from the air outlet, a main body, the light shield door being angularly movably supported on the main body, wherein a plurality of the light shield doors are formed substantially tabular and supported by the body about a rotational axis of the vertical direction, the ultraviolet lamp being provided on one side surface of each of the light shield doors, wherein the light shield door is angularly moved and held on the main body to expose the ultraviolet lamp outwardly when the ultraviolet radiation emitted from the ultraviolet lamp is to be radiated outwardly, and the light shield door is angularly moved and held on the main body to direct the ultraviolet lamp into the inner radiation chamber when the ultraviolet radiation emitted from the ultraviolet lamp is to be radiated into the inner radiation chamber.

If a room free of a person is to be sterilized by the ultraviolet pasteurizer, then the light shield door is opened and the ultraviolet lamp is energized to emit ultraviolet radiation. Since the ultraviolet radiation is radiated out of the ultraviolet pasteurizer, the ultraviolet pasteurizer can sterilize microorganisms attached to surrounding wall, ceiling, and floor surfaces and also microorganisms suspended in surrounding air.

If a room occupied by a person is to be sterilized by the ultraviolet pasteurizer, then the light shield doors are closed. The fan introduces external air from the air inlet into the inner radiation chamber, and flows near the ultraviolet lamp. The introduced air is thus sterilized by ultraviolet radiation emitted from the ultraviolet lamp. The sterilized air is then discharged from the air outlet. Microorganisms suspended in the air in the room can therefore be sterilized. Since the ultraviolet radiation emitted from the ultraviolet lamp is blocked by the light shield door and hence does not leak out of the ultraviolet pasteurizer, the ultraviolet pasteurizer can safely sterilize the occupied room.

Furthermore, when the light shield door is opened, since the light shield door is angularly moved to direct the ultraviolet lamp outwardly, the ultraviolet lamp is exposed outwardly and hence the ultraviolet radiation emitted therefrom is not blocked, consequently, the ultraviolet pasteurizer can sterilize a wide area uniformly.

There is also provided an ultraviolet pasteurizer according to the second aspect of the present invention, comprising an ultraviolet lamp, a light shield door openable and closable to block or pass ultraviolet radiation emitted from the ultraviolet lamp, an inner radiation chamber definable inwardly of the light shield door when ultraviolet is shut off from outward by the light shield, an air inlet and an air outlet providing communication between the inner radiation chamber and an external space, and a fan for introducing air from the external space via the air inlet into the inner radiation chamber, displacing the air near the ultraviolet lamp, and discharging the air from the air outlet, a main body, the light shield door being angularly movably supported on the main body, a plurality of planar rectangular light shield doors angularly movably coupled to each other at side edges thereof, and the ultraviolet lamp comprising a plurality of ultraviolet lamps mounted on respective sides of the light shield doors, wherein the side edges of the light shield doors are brought into abutment against each other with the ultraviolet lamps facing inwardly when the light shield doors are to be closed, and the side edges of the light shield doors are brought into abutment against each other with the ultraviolet lamps facing outwardly when the light shield doors are to be opened.

The side edges of the light shield doors are angularly movably coupled to each other. For opening the light shield doors, the side edges of the coupled light shield doors are brought into abutment against each other with the ultraviolet lamps facing outwardly. Since the ultraviolet lamps can radiate ultraviolet radiation in an angular range of 3600 in the circumferential direction, the ultraviolet pasteurizer can sterilize a wide area uniformly.

When the light shield doors are closed, the inner radiation chamber is defined in a space surrounded by the light shield doors. The ultraviolet lamps are accommodated in the inner radiation chamber. When air passes through the inner radiation chamber while the ultraviolet lamps are being turned on, the air can be sterilized. When the light shield doors are opened, the ultraviolet lamps are exposed. Therefore, the ultraviolet pasteurizer can sterilize surrounding wall, ceiling, and floor surfaces with ultraviolet radiation emitted from the exposed ultraviolet lamps. The range to which the ultraviolet radiation is applied can be adjusted by adjusting the degree of opening of the light shield doors. Thus, the ultraviolet pasteurizer can apply ultraviolet radiation only to a limited area which is free of persons.

According to the ultraviolet sterilizer of the second aspect of the present invention, the main body may preferably comprise a substantially triangular mount base disposed beneath the light shield doors, and the ultraviolet pasteurizer may further comprise a frame of substantially inverted U shape mounted on the mount base along one side thereof and extending upwardly, the light shield doors comprising three light shield doors which include a central light shield door having opposite side edges supported on the frame and held on the main body, and left and right light shield doors angularly movably mounted on the central light shield door by the frame.

Moreover, according to the ultraviolet pasteurizer of the second aspect of the present invention, the ultraviolet pasteurizer may preferably further comprise a power supply unit for supplying electric energy to the ultraviolet lamps and the fan, the power supply unit being disposed in a space surrounded by the light shield doors which are opened with the side edges held in abutment against each other so that the ultraviolet lamps face outwardly. When the light shield doors are opened to orient the ultraviolet lamps outwardly, a space is created by surfaces of the light shield doors which are free of the ultraviolet lamps. Since the power supply unit includes a transformer and other components, a space of certain size is required to accommodate the power supply unit therein. The power supply unit can be housed in the space thus created by the light shield doors. With the power supply unit housed in the space, the space can effectively be utilized, and hence the ultraviolet pasteurizer can be reduced in size.

BEST MODE FOR CARRYING OUT THE INVENTION

Embodiments of the present invention will hereinafter be described in detail with reference to the drawings FIGS. 1 through 7.

Figure 1:
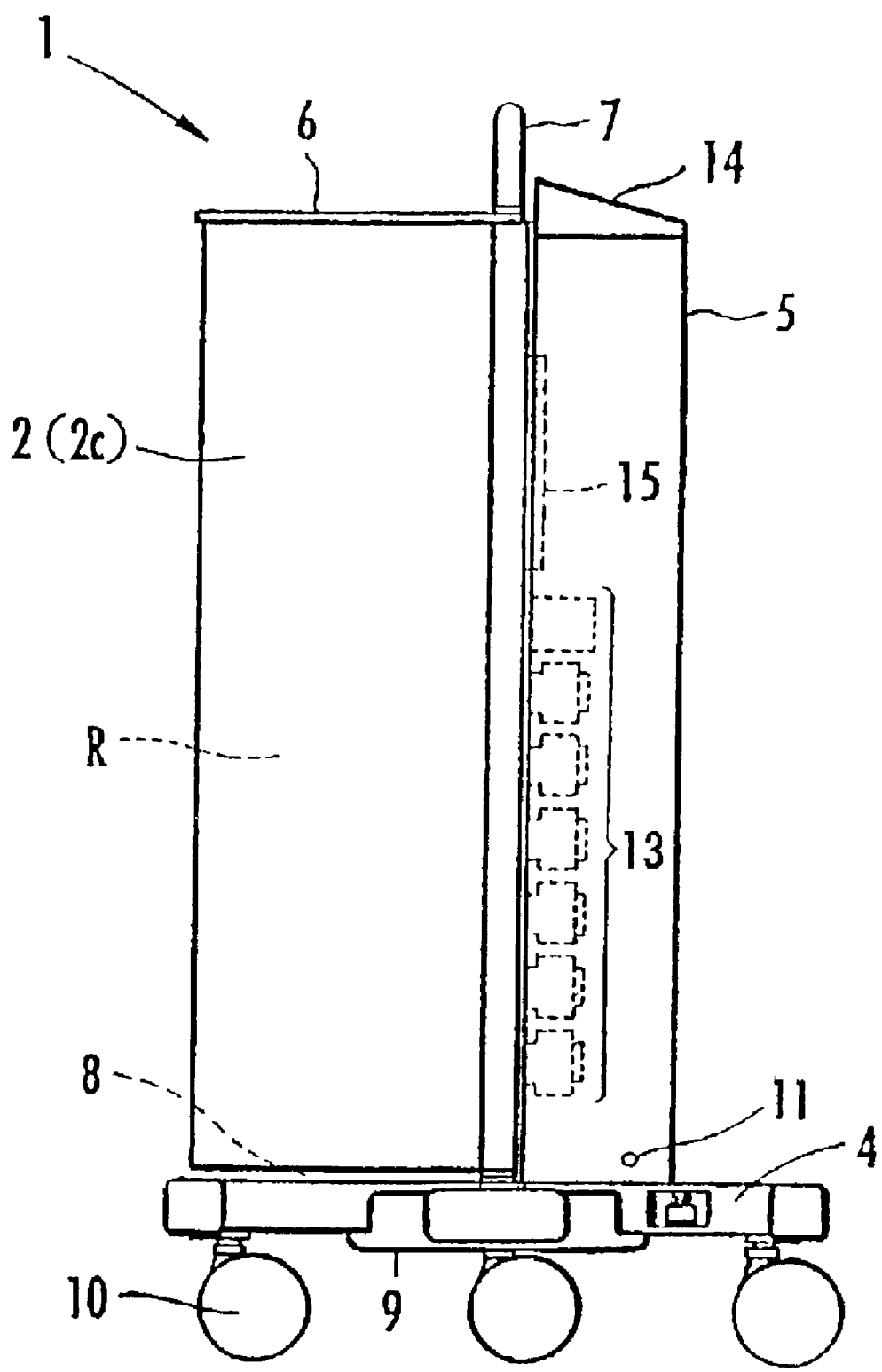
FIG. 1 is a side elevational view of an ultraviolet pasteurizer according to an embodiment of the present invention.
Figure 2:
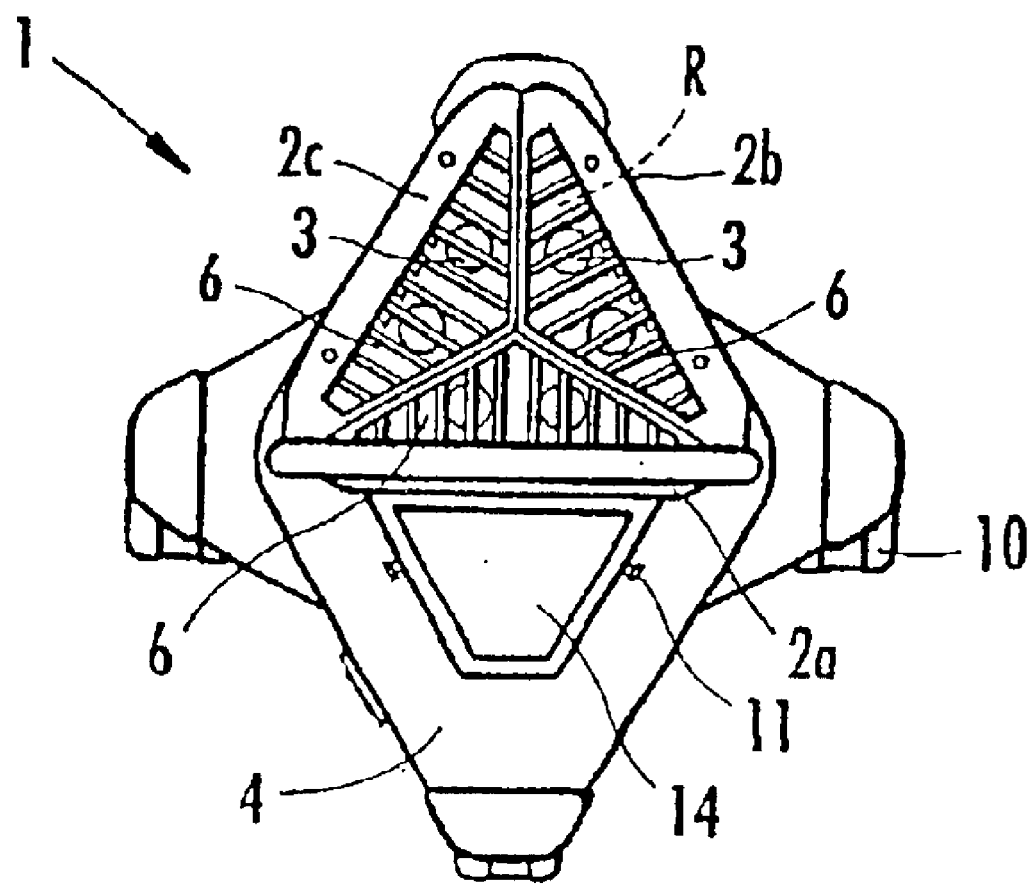
FIG. 2 is a plan view of the ultraviolet pasteurizer shown in FIG. 1.
Figure 3:
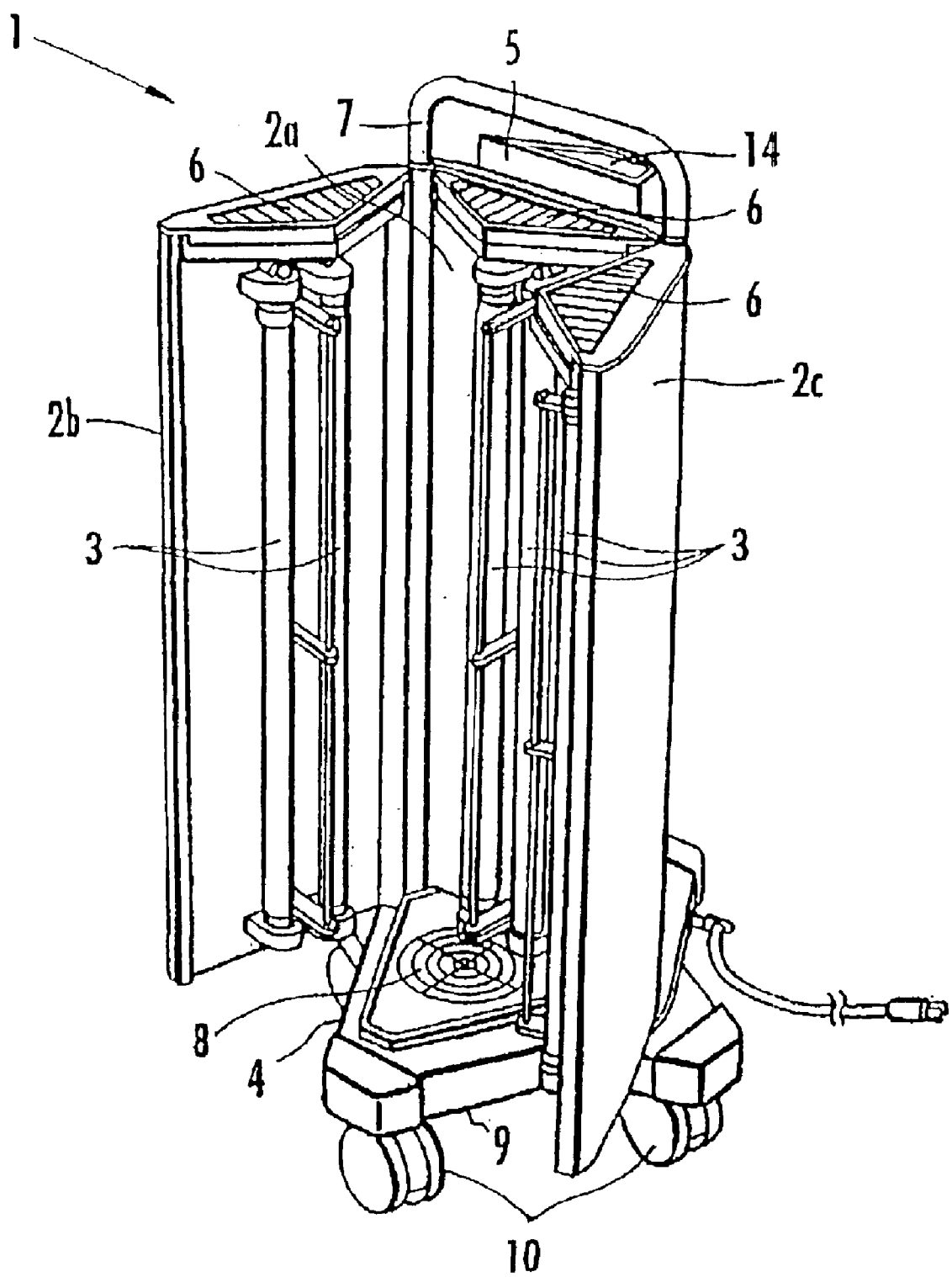
FIG. 3 is a perspective view of the ultraviolet pasteurizer shown in FIG. 1, with light shield doors being slightly open.

As shown in FIG. 1, an ultraviolet pasteurizer 1 according to an embodiment of the present invention has a light shield door assembly 2 housing ultraviolet lamps therein and disposed on a triangular mount base 4. The light shield door assembly 2 is angularly movably supported by a frame 7, described later on, and defines an inner radiation chamber R therein when the light shield door assembly 2 is closed as shown in FIG. 1. As shown in FIGS. 2 and 3, the light shield door assembly 2 comprises three planar rectangular light shield doors 2a, 2b, 2c. The ultraviolet pasteurizer 1 has a plurality of vertically elongate ultraviolet lamps 3 mounted on inner surfaces of the light shield doors 2a, 2b, 2c, with the central light shield door 2a fixedly mounted on the mount base 4, and a main case 5 mounted on the mount base 4 and disposed on a reverse side of the central light shield door 2a.

The light shield doors 2a, 2b, 2c have respective reflective plates of stainless steel on respective inner surfaces thereof. As shown in FIG. 3, two parallel ultraviolet lamps 3 are vertically mounted on the surface of each of the reflective plates. Each of the light shield doors 2a, 2b, 2c has an upper horizontal panel substantially in the shape of an isosceles triangle and has an air outlet 6 defined therein for ejecting air delivered from a fan 8, described later on. The air outlets 6 of the light shield doors 2a, 2b, 2c are arranged to block ultraviolet radiation emitted from the ultraviolet lamps 3 against leakage out of the inner radiation chamber R. Of the light shield doors 2a, 2b, 2c, the central light shield door 2a is fixed to the frame 7, which is of a substantially inverted U shape, extending upwardly from the mount base 4. The left and right light shield doors 2b, 2c have side edges angularly supported on respective opposite side edges of the central light shield door 2a by the frame 7. When the light shield doors 2a, 2b, 2c are closed with the ultraviolet lamps 3 disposed inside, the inner radiation chamber R is defined in a space surrounded by the light shield doors 2a, 2b, 2c, as shown in FIGS. 1 and 2. The frame 7 has an upper end for use as a handle to be gripped by the user when the ultraviolet pasteurizer 1 is carried.

Figure 4:
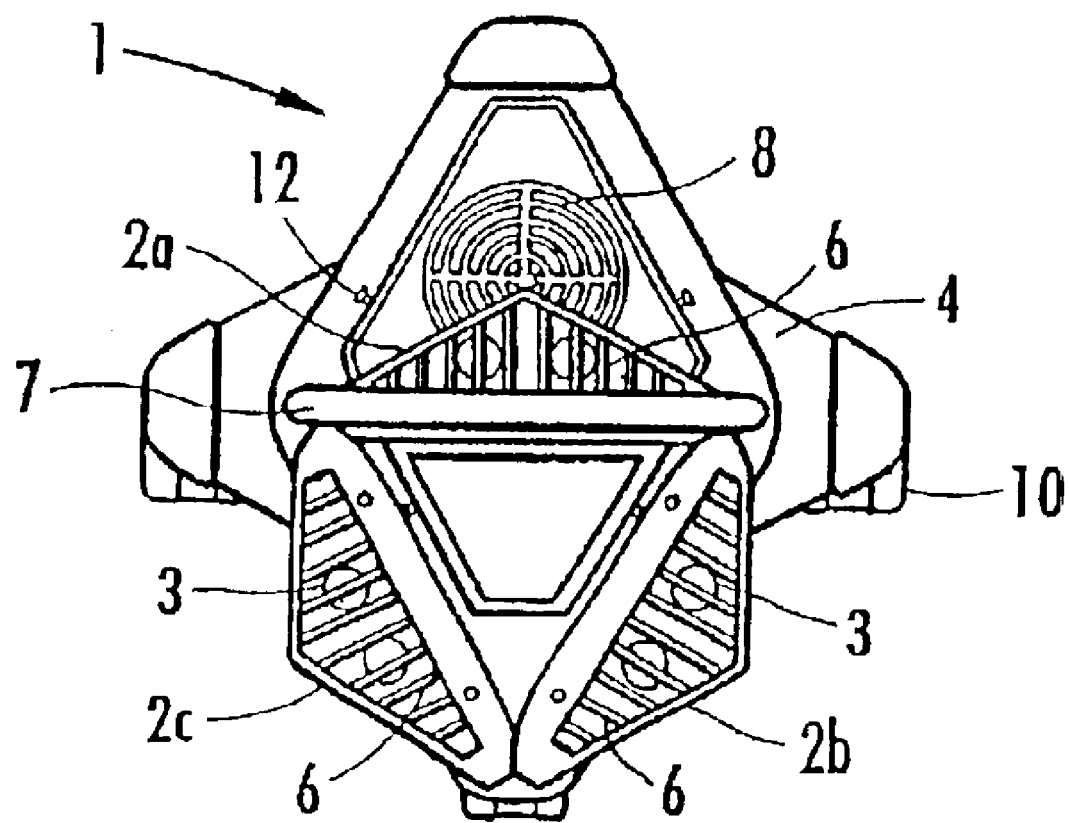
FIG. 4 is a plan view of the ultraviolet pasteurizer shown in FIG. 1, with the light shield doors being fully open.

As shown in FIG. 3, the fan 8 is mounted in the mount base 4 near the inner surface of the central light shield door 2a. The mount base 4 has an air inlet 9 defined in the bottom thereof below the fan 8 for drawing external air into the inner radiation chamber R. In the present embodiment, an ozone generator (not shown) for generating ozone is disposed between the air inlet 9 and the fan 8. The main case 5 is disposed on the outer surface of the central light shield door 2a. Casters 10 are mounted on the bottom of the mount base 4 for making the ultraviolet pasteurizer 1 movable. As shown in FIG. 2, the mount base 4 supports two door opening detecting switches 11 which can be turned on by being pushed by the light shield doors 2b, 2c when the light shield doors 2b, 2c are opened. As shown in FIG. 4, the mount base 4 also supports two door closing detecting switches 12 which can be turned on by being pushed by the light shield doors 2b, 2c when the light shield doors 2b, 2c are closed.

The main case 5 is of a substantially trapezoidal shape as viewed in plan such that the main case 5 is neatly accommodated within the light shield doors 2a, 2b, 2c that are shaped into a substantially triangular prism when the left and right light shield doors 2b, 2c are opened with their ultraviolet lamps 3 facing outwardly, as shown in FIG. 4. As shown in FIG. 1, the main case 5 houses therein a power supply unit 13 for supplying electric energy to the ultraviolet lamps 3, the fan 8, and the ozone generator. The main case 5 has on its upper surface a control panel 14 for setting operating conditions for the ultraviolet pasteurizer 1. As shown in FIG. 1, the main case 5 also houses therein a controller 15 for controlling operating conditions for the ultraviolet pasteurizer 1.

Modes of use of the ultraviolet pasteurizer 1 will be described below with reference to FIGS. 2 and 4.

First, a mode for sterilizing a room free of persons will be described below. When the ultraviolet pasteurizer 1 is to be used in an unoccupied place, the left and right light shield doors 2b, 2c are opened laterally to place their ultraviolet lamps 3 facing outwardly. When the light shield doors 2b, 2c are fully folded back, the door opening detecting switches 11 are turned on, whereupon the controller 15 detects the full opening of the light shield doors 2b, 2c. In the present embodiment, the ultraviolet lamps 3 can be energized when both the opening detecting switches 11 are turned on.

Then, when an operation switch (not shown) on the control panel 14 is turned on with the light shield doors 2a, 2b, 2c being fully open, an operation start timer is actuated, and the ultraviolet lamps 3 are then energized after elapse of 5 minutes. When the ultraviolet lamps 3 are energized, they emit ultraviolet radiation to sterilize microorganisms attached to indoor walls, ceiling, and floor to which the ultraviolet radiation is applied, the ultraviolet radiation emitted from the ultraviolet lamps 3 also sterilizes microorganisms suspended in the air in the room.

A mode for sterilizing a room occupied by persons will be described below. In such a room, no ultraviolet radiation should be radiated out of the ultraviolet pasteurizer 1. Therefore, the ultraviolet pasteurizer 1 is used with the light shield doors 2a, 2b, 2c being closed. First, as shown in FIG. 2, the left and right light shield doors 2b, 2c are closed with their ultraviolet lamps 3 facing inwardly until the light shield doors 2a, 2b, 2c are brought into a substantially triangle prism, whereupon the inner radiation chamber R is formed in the space surrounded by the light shield doors 2a, 2b, 2c. At this time, the door closing detecting switches 12 are turned on, allowing the controller 15 to detect the fully closure of the light shield doors 2b, 2c. In the present embodiment, the ultraviolet lamps 3 can be energized when both the door closing detecting switches 12 are turned on.

When the operation switch on the control panel 14 is turned on with the light shield doors 2a, 2b, 2c being closed, the ultraviolet lamps 3 and the fan 8 start operating. When the fan 8 operates, it draws external air from the air inlet 8, and discharges the drawn air through the inner radiation chamber R from the air outlet 6. At this time, the air passing through the inner radiation chamber R is sterilized by the ultraviolet radiation emitted from the light shield doors 2a, 2b, 2c. Therefore, microorganisms suspended in the air in the room are sterilized. In the present embodiment, since the ozone generator, not shown, is incorporated in the ultraviolet pasteurizer 1, the ultraviolet pasteurizer 1 can not only sterilize the air in the room, but also deodorize the air in the room.

In the above embodiment, the ultraviolet lamps 3 are energized only when the light shield doors 2a, 2b, 2c are fully opened or fully closed. However, the ultraviolet lamps 3 may be made energizable when only one of the light shield doors 2a, 2b, 2c is opened and the others are closed. For example, even when a room is occupied by a person, the ultraviolet pasteurizer 1 can direct ultraviolet radiation toward an area free of the person to sterilize indoor walls, ceiling, and floor in that area.

In the above embodiment, the light shield doors 2a, 2b are angularly movably coupled to each other and the light shield doors 2a, 2c are angularly movably coupled to each other, and when the left and right light shield doors 2b, 2c are angularly moved to open or close the light shield doors 2a, 2b, 2c. However, the light shield doors 2a, 2b are angularly movably coupled to each other and the light shield doors 2b, 2c may be angularly movably coupled to each other at their side edges.

Figure 5:
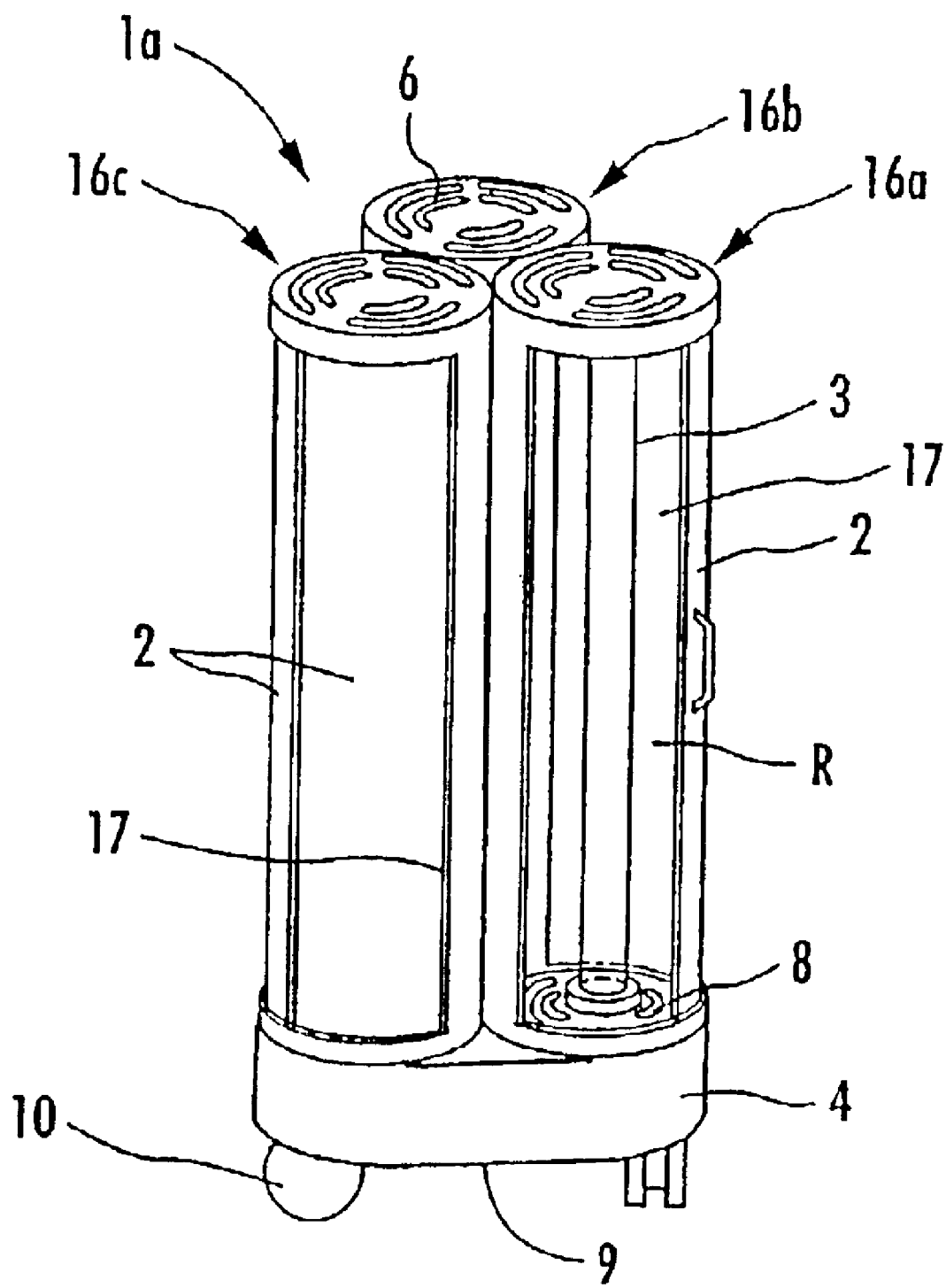
FIG. 5 is a perspective view of an ultraviolet pasteurizer according to another embodiment of the present invention.

An ultraviolet pasteurizer according to another embodiment of the present invention will be described below with reference to FIG. 5. Those parts of the ultraviolet pasteurizer shown in FIG. 5 which are identical to those of the ultraviolet pasteurizer shown in FIGS. 1 through 4 are denoted by identical reference characters, and will not be described in detail below. As shown in FIG. 5, an ultraviolet pasteurizer 5a has substantially cylindrical tubular members 16a, 16b, 16c vertically mounted on a mount base 4. The tubular members 16a, 16b, 16c accommodate respective vertically elongate ultraviolet lamps 3 therein. The tubular members 16a, 16b, 16c have respective vertically elongate openings 17 defined therein which extend about 120° in the circumferential direction. Each of the openings 17 can be opened and closed by two light shield doors 2. The light shield doors 2 are slidable in the circumferential direction along the opening 17 to open and close the opening 17. When the light shield doors 2 are closed, each of the tubular members 16a, 16b, 16c defines an inner radiation chamber R therein. The mount base 4 has an air inlet 9 defined therein below the tubular members 16a, 16b, 16c for introducing air to be drawn by fans 8 housed in the mount base 4. The tubular members 16a, 16b, 16c have air outlets 6 defined in upper ends thereof for discharging air that has passed upwardly through the tubular members 16a, 16b, 16c.

The ultraviolet pasteurizer 1a operates as follows: When the openings 17 in the three tubular members 16a, 16b, 16c are opened and the ultraviolet lamps 3 are energized, the ultraviolet pasteurizer 1a emits ultraviolet radiation therearound to sterilize surrounding wall, ceiling, and floor surfaces. Alternatively, the opening 17 in the tubular member 16a may be opened and the openings 17 in the other tubular members 16b, 16c may be closed to apply ultraviolet radiation to only a limited indoor area to sterilize wall, ceiling, and floor surfaces therein. At the same time, the fans 8 in the other tubular members 16b, 16c are operated, and the ultraviolet lamps 3 in these tubular members 16b, 16c are energized to emit ultraviolet radiation in the inner radiation chamber R. Since air drawn from the air inlet 9 is sterilized in the inner radiation chamber R and then discharged from the air outlet 6, the air in the room can also be sterilized.

Figure 6:
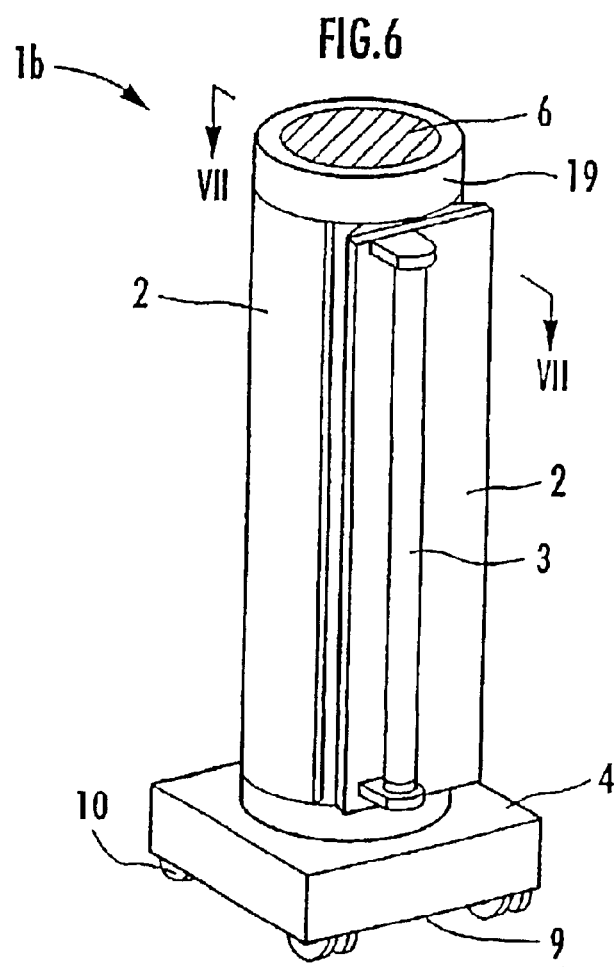
FIG. 6 is a perspective view of an ultraviolet pasteurizer with four light shield doors according to still another embodiment of the present invention.
Figure 7:
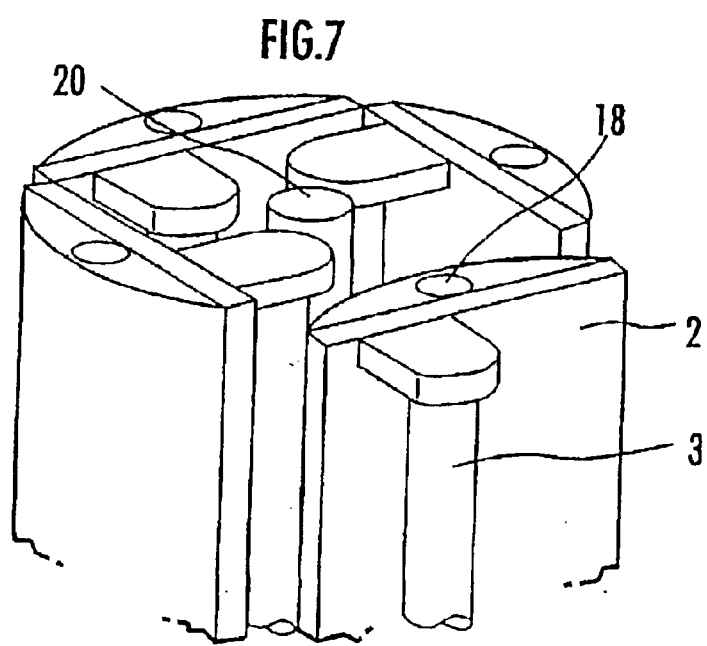
FIG. 7 is an enlarged fragmentary perspective view of the ultraviolet pasteurizer shown in FIG. 6, partly in cross section taken along line VII—VII of FIG. 6.

An ultraviolet pasteurizer with four light shield doors according to still another embodiment of the present invention will be described below with reference to FIGS. 6 and 7. Those parts of the ultraviolet pasteurizer shown in FIGS. 6 and 7 which are identical to those of the ultraviolet pasteurizer shown in FIGS. 1 through 5 are denoted by identical reference characters, and will not be described in detail below. As shown in FIGS. 6 and 7, an ultraviolet pasteurizer 1b is of a cylindrical shape in its entirety and has four light shield doors 2 which support respective ultraviolet lamps 3. Each of the light shield doors 2 is angularly movable about 180° about a vertical shaft 18. In FIGS. 6 and 7, only one of the light shield doors 2 is angularly moved to have its ultraviolet lamp 3 exposed outwardly. A mount base 4 houses a fan (not shown) housed therein, and has an air inlet 9 defined in the bottom thereof. The four light shield doors 2 have respective upper ends pivotally supported by an upper case 19 having an air outlet 6 defined therein. The upper case 19 is coupled to the mount base 4 by a vertical central shaft 20 shown in FIG. 7.

The ultraviolet pasteurizer 1b operates as follows: When all the four light shield doors 2 are turned to have their ultraviolet lamps 3 exposed outwardly, the ultraviolet pasteurizer 1b emits ultraviolet radiation therearound to sterilize surrounding wall, ceiling, and floor surfaces. Alternatively, when only one of the light shield doors 2 is turned to expose its ultraviolet lamp 3 outwardly, as shown in FIGS. 6 and 7, only the outwardly facing the ultraviolet lamp 3 emits ultraviolet radiation outwardly to apply ultraviolet radiation to only a limited indoor area to sterilize wall, ceiling, and floor surfaces therein. When all the light shield doors 2 are closed, ultraviolet radiation is emitted from all the ultraviolet lamps 3 into the inner radiation chamber R surrounded by the light shield doors 2. The fan housed in the mount base 4 introduces external air from the air inlet 9. The introduced air flows upwardly through the inner radiation chamber R, is sterilized by the ultraviolet radiation emitted from the ultraviolet lamps 3, and is then discharged from the air outlet 6.

In the above embodiments, the ultraviolet pasteurizer has three or four light shield doors. However, the ultraviolet pasteurizer may have two or five or more light shield doors. For example, the central light shield door 2a may be dispensed with, and an ultraviolet lamp 3 may be mounted on the back of the main case 5, with only two left and right light shield doors 2b, 2c being used as light shield doors. If a plurality of light shield doors are angularly movably coupled at side edges thereof, they may be directly coupled to each other or may be coupled by a connecting member such as the frame 7.

INDUSTRIAL APPLICABILITY

The present invention is useful as an ultraviolet pasteurizer for sterilizing an indoor space by the application of ultraviolet radiation.

What is claimed is:

1. An ultraviolet pasteurizer comprising:
   an ultraviolet lamp;
   a light shield door having the ultraviolet lamp mounted thereon, said light shield door being openable and closable to block or pass ultraviolet radiation emitted from said ultraviolet lamp;
   an inner radiation chamber definable inwardly of said light shield door when said light shield door is closed;
   an air inlet and an air outlet providing communication between said inner radiation chamber and an external space;
   a fan for introducing air from the external space via said air inlet into said inner radiation chamber, displacing the air near said ultraviolet lamp, and discharging the air from said air outlet; and
   a main body, said light shield door being angularly movably supported on said main body,
   the arrangement being such that when the ultraviolet radiation emitted from said ultraviolet lamp is to be radiated outwardly, said light shield door is angularly moved and held on said main body to expose said ultraviolet lamp outwardly, and
   when the ultraviolet radiation emitted from said ultraviolet lamp is to be radiated into said inner radiation chamber, said light shield door is angularly moved and held on said main body to direct said ultraviolet lamp into said inner radiation chamber.

2. An ultraviolet pasteurizer according to claim 1, wherein said light shield door comprises a plurality of planar, substantially rectangular light shield doors angularly movably coupled to each other at side edges thereof, and said ultraviolet lamp comprises a plurality of ultraviolet lamps mounted on respective sides of said light shield doors, the arrangement being such that when said light shield doors are to be closed, the side edges of the light shield doors of both ends are brought into abutment against each other with the ultraviolet lamps facing inwardly, and when said light shield doors are to be opened, the side edges of the light shield doors of both ends are brought into abutment against each other with the ultraviolet lamps facing outwardly.

3. An ultraviolet pasteurizer according to claim 2, wherein said main body comprises a substantially triangular mount base disposed beneath said light shield doors, further comprising a frame of substantially inverted U shape mounted on said mount base along one side thereof and extending upwardly, said light shield doors comprising three light shield doors which include a central light shield door having opposite side edges supported on said frame and held on said main body, and left and right light shield doors angularly movably mounted on said central light shield door by said frame.

4. An ultraviolet pasteurizer according to claim 2 or 3, further comprising:
   a power supply unit for supplying electric energy to said ultraviolet lamps and said fan, said power supply unit being disposed in a space surrounded by the light shield doors, the left and the right light shield doors which are movable having the side edges held in abutment against the central light shield door so that said ultraviolet lamps face outwardly.

5. The ultraviolet pasteurizer according to claim 1, further comprising a door closing detecting switch and a door opening detecting switch for detecting the position of the at least one movable light shield door, wherein the ultraviolet lamps are energized only when the at least one movable light shield door is either fully closed or fully opened.

6. The ultraviolet pasteurizer according to claim 1, further comprising a control panel on a upper surface of the pasteurizer for setting operating conditions of the pasteurizer.

7. The ultraviolet pasteurizer according to claim 3, further comprising a wheel attached to the mount base for making the pasteurizer movable.

8. An ultraviolet pasteurizer comprising:
   an ultraviolet lamp;
   a light shield door openable and closable to block or pass ultraviolet radiation emitted from said ultraviolet lamp;
   a tubular-shaped inner radiation chamber definable inwardly of said light shield door when said light shield door is closed; an air inlet and an air outlet providing communication between said inner radiation chamber and an external space;
   a fan for introducing air from the external space via said air inlet into said inner radiation chamber, displacing the air near said ultraviolet lamp, and discharging the air from said air outlet, the light shield door being slidable in a circumferential direction along an opening in the tubular-shaped radiation chamber to open and close the opening; and
   a plurality of tubular-shaped inner radiation chambers, the plurality of tubular radiation chambers each being mounted on a common base.

9. The ultraviolet pasteurizer according to claim 8, further comprising a wheel attached to the common base for making the pasteurizer movable.

10. An ultraviolet pasteurizer comprising:
    an ultraviolet lamp;
    a light shield door openable and closable to block or pass ultraviolet radiation emitted from said ultraviolet lamp;
    an inner radiation chamber definable inwardly of said light shield door when said light shield door is closed; an air inlet and an air outlet providing communication between said inner radiation chamber and an external space;
    a fan for introducing air from the external space via said air inlet into said inner radiation chamber, displacing the air near said ultraviolet lamp, and discharging the air from said air outlet, the light shield door, the light shield door being rotatable by 180° about an axis extending vertically through a central portion of the light shield door; and a main body, said light shield door being rotabably movably supported on said main body, said ultraviolet lamp being mounted on said light shield door, the arrangement being such that when the ultraviolet radiation emitted from said ultraviolet lamp is to be radiated outwardly, said light shield door is rotatably moved and held on said main body to expose said ultraviolet lamp outwardly, and when the ultraviolet radiation emitted from said ultraviolet lamp is to be radiated into said inner radiation chamber, said light shield door is rotatably moved and held on said main body to direct said ultraviolet lamp into said inner radiation chamber.

11. An ultraviolet pasteurizer comprising:

an ultraviolet lamp;

a light shield door openable and closable to block or pass ultraviolet radiation emitted from said ultraviolet lamp;

an inner radiation chamber definable inwardly of said light shield door when said light shield door is closed;

an air inlet and an air outlet providing communication between said inner radiation chamber and an external space; and a fan for introducing air from the external space via said air inlet into said inner radiation chamber, displacing the air near said ultraviolet lamp, and discharging the air from said air outlet, the light shield door, the light shield door being rotatable by 180° about an axis extending vertically through a central portion of the light shield door, wherein said light shield door comprises a plurality of planar, substantially rectangular light shield doors angularly movably coupled to each other at side edges thereof, and said ultraviolet lamp comprises a plurality of ultraviolet lamps mounted on respective sides of said light shield doors, the arrangement being such that when said light shield doors are to be closed, the side edges of the light shield doors are brought into abutment against each other with the ultraviolet lamps facing inwardly, and when said light shield doors are to be opened, the side edges of the light shield doors are brought into abutment against each other with the ultraviolet lamps facing outwardly.

12. An ultraviolet pasteurizer according to claim 1, wherein three light shield doors are provided that are openable and closable to block or pass ultraviolet radiation emitted from the ultraviolet lamps.

13. An ultraviolet pasteurizer according to claim 1, wherein a triangular-shaped inner radiation chamber is definable inwardly of the light shield door when the light shield door is closed.

* * * * *